United States Patent [19]

Beljanski

[11] Patent Number: 5,145,839

[45] Date of Patent: Sep. 8, 1992

[54] PHARMACEUTICAL COMPOSITION AND METHOD OF USE

[76] Inventor: Mirko Beljanski, 46, Boulevard de Port Royal, 75005 Paris, France

[21] Appl. No.: 365,047

[22] Filed: Jun. 9, 1989

[30] Foreign Application Priority Data

Jun. 23, 1988 [FR] France .................. 88 08434

[51] Int. Cl.⁵ ................ A61K 31/35; A61K 31/70
[52] U.S. Cl. .................... 514/27; 514/456; 536/4.1; 536/18.1
[58] Field of Search ............ 514/27, 456; 536/4.1, 536/18.1

[56] References Cited

U.S. PATENT DOCUMENTS

| | | | |
|---|---|---|---|
| 3,903,266 | 9/1975 | Robbins | 514/56 |
| 4,238,483 | 12/1980 | Frazier | 514/25 |
| 4,264,729 | 4/1981 | Beljanski | 435/6 |
| 4,297,348 | 10/1981 | Frazier | 514/27 |

FOREIGN PATENT DOCUMENTS 2117727 7/1972 France .
2426698 1/1980 France .

OTHER PUBLICATIONS

Suolinna et al.; Cancer Research, 35(7):1865–1872 (1975).
Takase et al.; Chemical Abstracts, 109(1):810h (1987).
Ono et al.; Eur. J. Biochem., 190:469–476, (Jul. 5, 1990).

*Primary Examiner*—Ronald W. Griffin
*Assistant Examiner*—Nancy S. Carson
*Attorney, Agent, or Firm*—Roland Plottel

[57] ABSTRACT

Naringin and naringenin are disclosed as pharmaceuticals that selectively inhibit the growth of cancer cells in the presence of normal cells. They are also effective against cancer cells that are resistant to chemotherapy or radiotherapy. It is shown that naringin and naringenin selectively contract DNA chains of tumor cells but not DNA chains of normal cells. The subject compounds also exhibit anti-viral activity. A novel method for the recovery of naringin and naringenin from natural vegetable sources is taught.

8 Claims, 14 Drawing Sheets

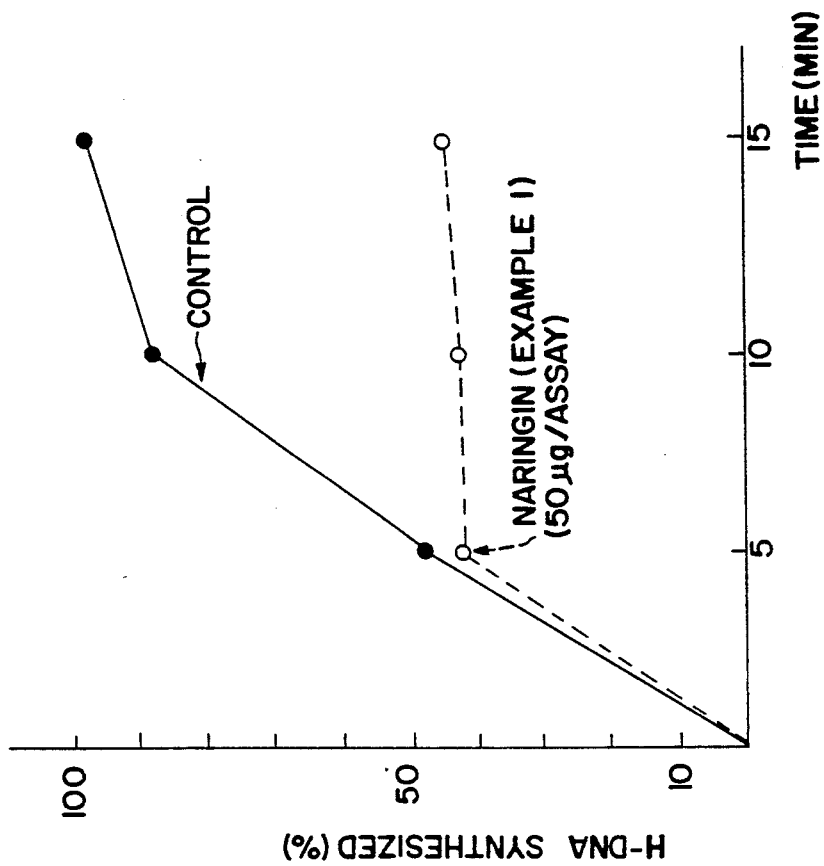
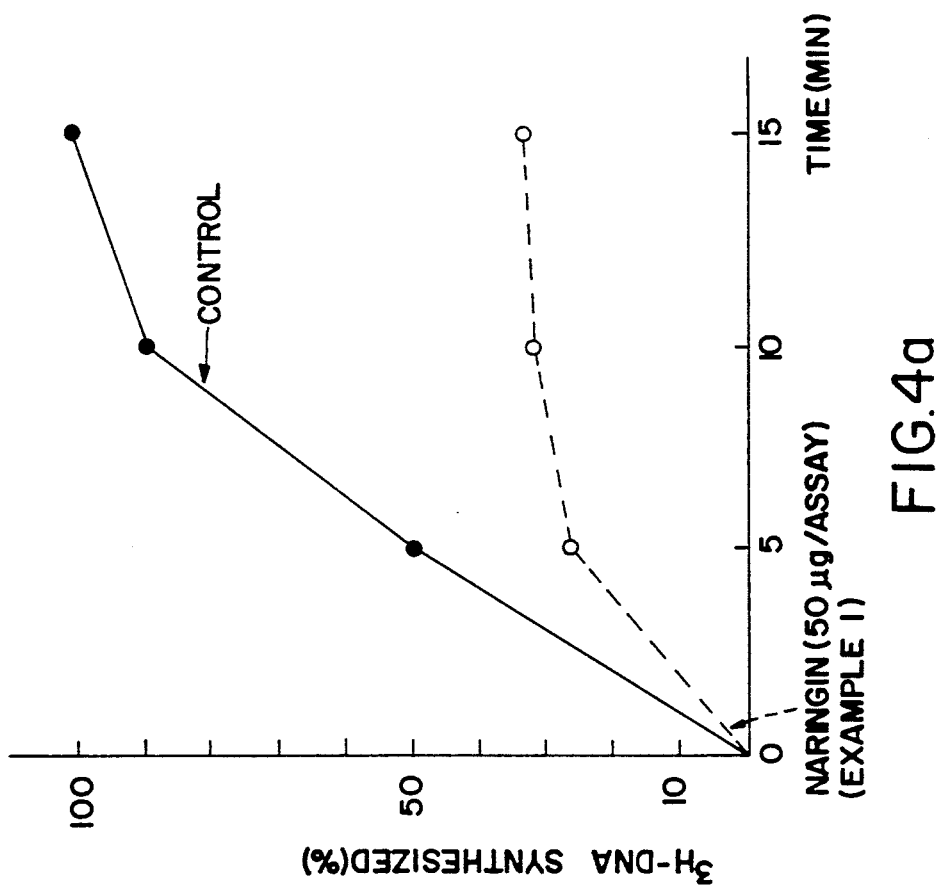

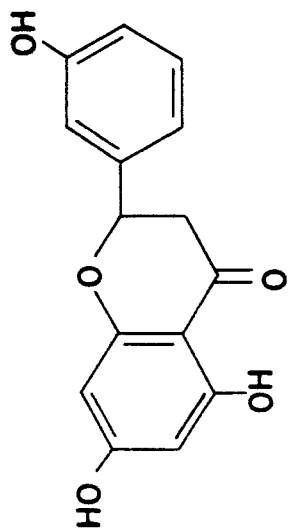
FIG.8b NARINGENIN
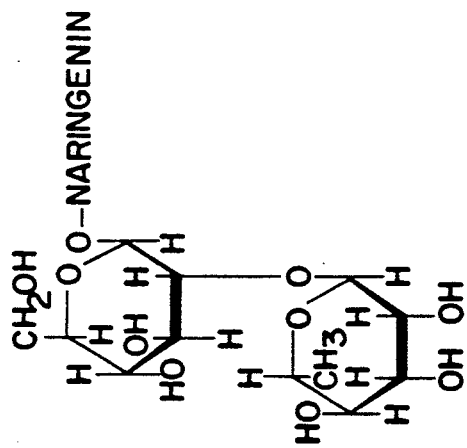
FIG.8a NARINGIN

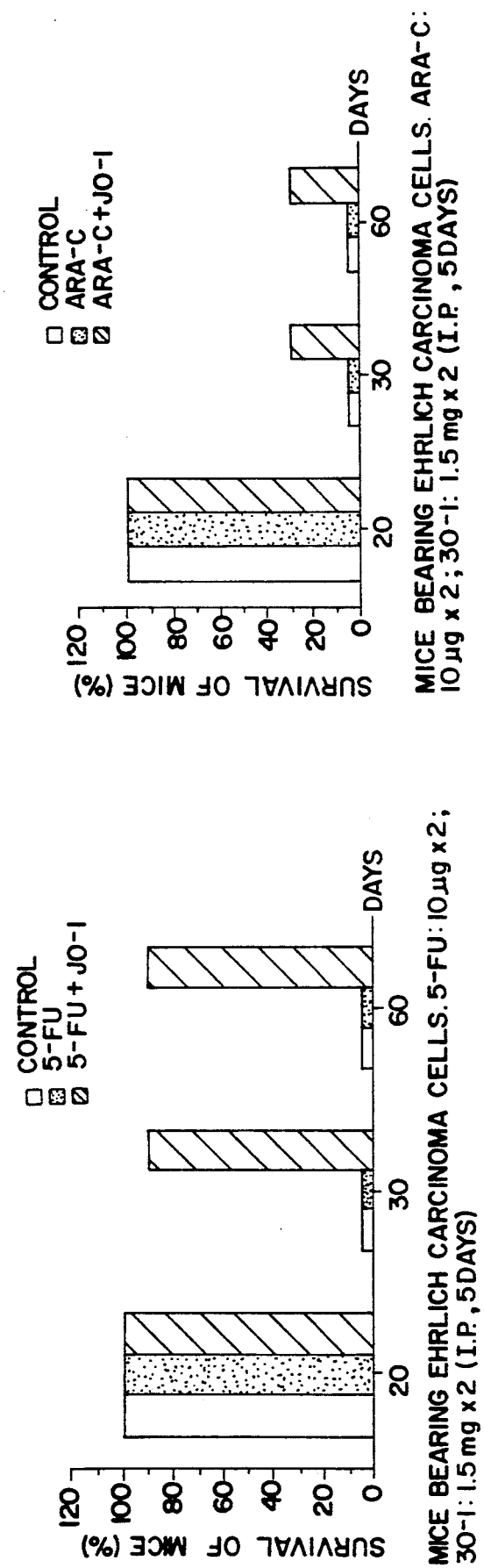

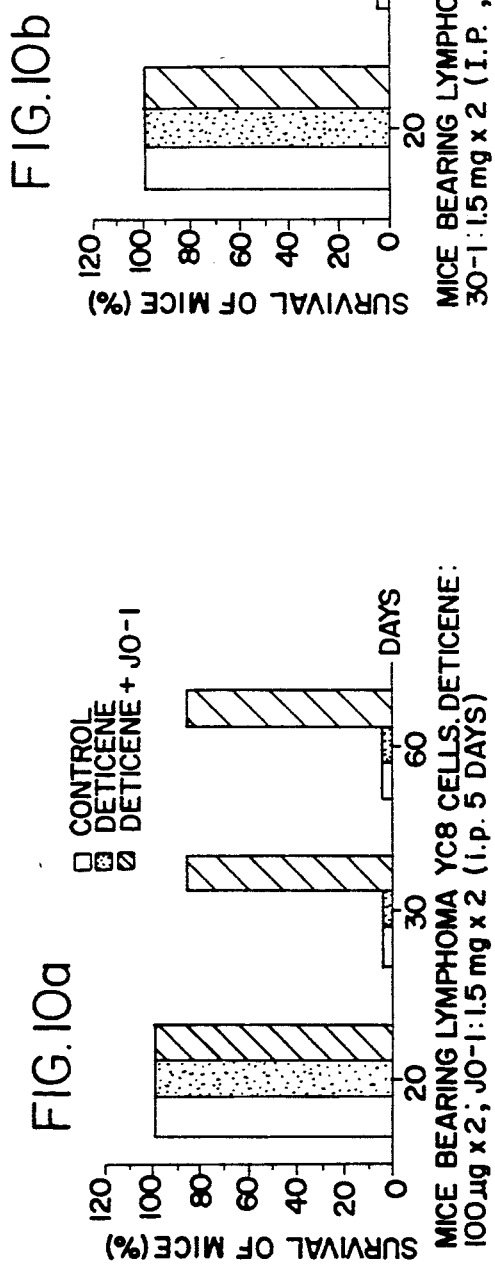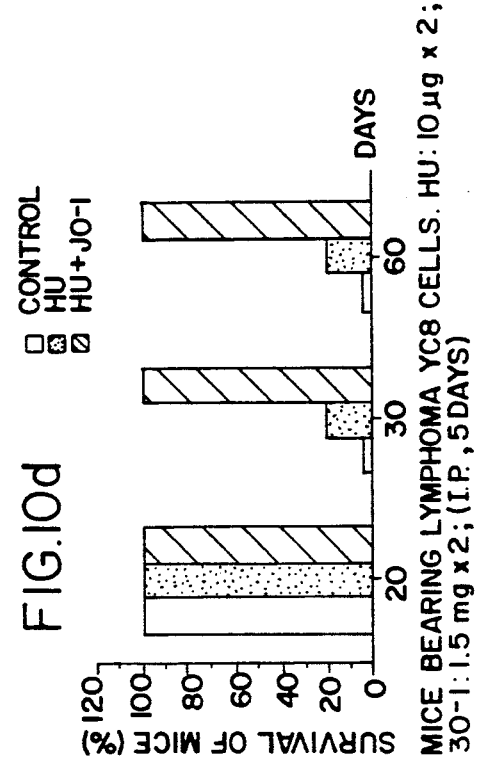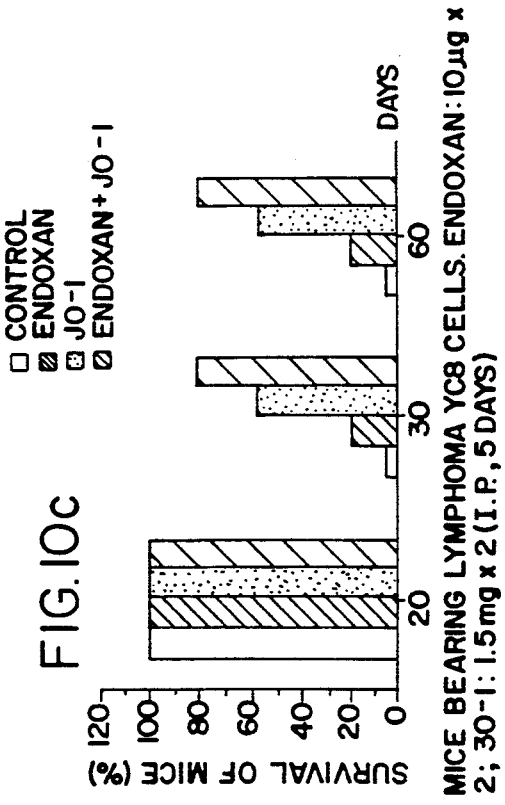

| SURVIVAL DAYS | UNTREATED | COMMERCIAL NARINGIN 2mg x 2/DAY | | NARINGIN EXAMPLE I 2mg x 2/DAY | |
|---|---|---|---|---|---|
| | | | SURVIVAL % | | SURVIVAL % |
| 0 | 10 | 10 | 100 | 10 | 100 |
| 10 | 10 | 10 | 100 | 10 | 100 |
| 15 | 7 | 8 | 80 | 10 | 100 |
| 20 | 2 | 5 | 50 | 8 | 80 |
| 25 | 0 | 5 | 50 | 7 | 70 |
| 30 | 0 | 5 | 50 | 7 | 70 |

FIG. 11

| SURVIVAL (DAYS) | UNTREATED | NARINGIN (EXAMPLE 1) 3mg x 2/DAY FOR 15 DAYS | SURVIVAL % |
|---|---|---|---|
| 0 | 20 | 20 | 100 |
| 10 | 20 | 20 | 100 |
| 20 | 12 | 20 | 100 |
| 25 | 0 | 17 | 85 |
| 60 | 0 | 17 | 85 |

FIG.12

|  |  | NARINGIN (EXAMPLE 1) | | | |
|---|---|---|---|---|---|
| SURVIVAL DAYS | UNTREATED | 1.5 mg x 2/DAY SURVIVAL | % | 3.0 mg x 2/DAY | SURVIVAL % |
| 0 | 10 | 10 | 100 | 10 | 100 |
| 10 | 10 | 10 | 100 | 10 | 100 |
| 15 | 8 | 4 | 40 | 10 | 100 |
| 20 | 4 | 4 | 40 | 7 | 70 |
| 25 | — | 4 | 40 | 5 | 50 |
| 30 | 0 | 4 | 40 | 5 | 50 |

FIG.13

| SURVIVAL (DAYS) | UNTREATED | COMMERCIAL NARINGENIN | | | |
|---|---|---|---|---|---|
| | | 0.5 mg x 2/DAY | SURVIVAL % | 1mg x 2/DAY | SURVIVAL % |
| 0 | 10 | 10 | 100 | 10 | 100 |
| 10 | 10 | 10 | 100 | 10 | 100 |
| 15 | 10 | 10 | 100 | 10 | 80 |
| 20 | 6 | 7 | 70 | 8 | 50 |
| 25 | 2 | 3 | 30 | 5 | 50 |
| 30 | 0 | 3 | 30 | 5 | 50 |

FIG. 14

PHARMACEUTICAL COMPOSITION AND METHOD OF USE

BACKGROUND OF THE INVENTION

The number of solid cancers and lymphoid or blood cancers is stagnant and/or rises and chemotherapic treatments provide disappointing or very insufficient results. The major difficulty comes from the fact that chemotherapeutic agents are toxic and sometimes lethal. They inhibit the proliferation not only of malignant cells but also that of normal cells which makes it necessary to find selective agents, capable of acting by themselves or in combination, in order that the inhibiting erect toward undesirable cells predominates. Having at disposition agents that are highly selective so that side effects are held to the minimum is an important objective of cancer research.

The same problem of poor selectivity and undesirable side effects occurs in the application of radiotherapy.

Considerable efforts are also given to find chemical entities that would be active against viruses that cause diseases in humans, animals and plants. The known antiviral entities also are not sufficiently selective; in addition their number is much smaller than those known to be active against bacteria and fungi.

In the case of both malignancies and viruses, it would be desirable to find entities that are active and selective at the level of abnormal cells, e.g. that will usefully affect DNA or enzymes implicated in the proliferation of malignant or virus infected cells.

BRIEF DESCRIPTION OF THE INVENTION

I have found that naringin and naringenin, and pharmaceutically acceptable derivatives thereof, inhibit the growth of cancer cells. I have also found that these compounds do not substantially damage normal cells. This selectivity between cancerous and non-cancerous cells makes naringin and naringenin effective therapeutic agents for the treatment of cancers.

In preferred embodiments, naringin, naringenin, or a pharmaceutically acceptable ester or salt thereof, or mixtures of one or more of the foregoing, are admixed with a pharmaceutically acceptable carrier. The resulting pharmaceutical composition is then separated into unit dosages, and one or more units is administered to the patient at a given time. The dosage, manner of administration, and frequency and length of time for treatment, vary with the patient, and are chosen by the physician to assure the best contact of the cancerous cells with an effective concentration of the agent.

In another aspect of the invention, a patient whose cancer cells are resistant to chemotherapy or radiotherapy is treated with an agent of this invention. I have found that these agents can be effective even against cancer cells which are resistant to chemotherapy and/or radiotherapy.

In still another aspect of the invention, it has been found that naringin and naringenin and their derivatives exhibit a synergistic effect when administered to animals or to patients undergoing conventional chemotherapy.

Another aspect of the invention resides in the discovery that naringin and naringenin provoke the contraction, i.e. closing, of DNA chains of cancer cells but not that of DNA chains of normal cells. The agents of this invention act on initiation sites of DNA of cancer cells, and also prevent the DNA chain elongation. It is believed that this causes in totality or partly the inhibition of growth of cancer cells. The closing of DNA chains prevents or inhibits the addition of deoxyribonucleotide units into the DNA molecule.

The fact that naringin and naringenin contract DNA chains from cancer cells suggests that in the acquired immune deficiency syndrome (AIDS) disease, induced by HIV virus, naringin and naringenin may prevent the formation of viral particles from "protooncogenes" which must modified during infection in order to produce virus. Thus, naringin and naringenin and their derivatives may be of value in the treatment of AIDS.

As far as planar and animal viral injection is concerned, naringin and naringenin administered to the host inhibit viral proliferation. This is believed due to their inhibiting the activity of certain enzymes present in or produced by the virus.

Yet another embodiment of the invention comprises a method for extraction of naringin and naringenin from natural vegetable (plant) sources.

THE DRAWINGS

FIGS. 4a and 4b show the effect of naringin on the synthesis in vitro of DNA from cancer cells, when added at the start of synthesis and when added a period of time after the synthesis reaction has started.

FIGS. 8a and 8b show the structural formulae of naringin and naringenin, born being compounds known in the chemical literature.

Figure 1:
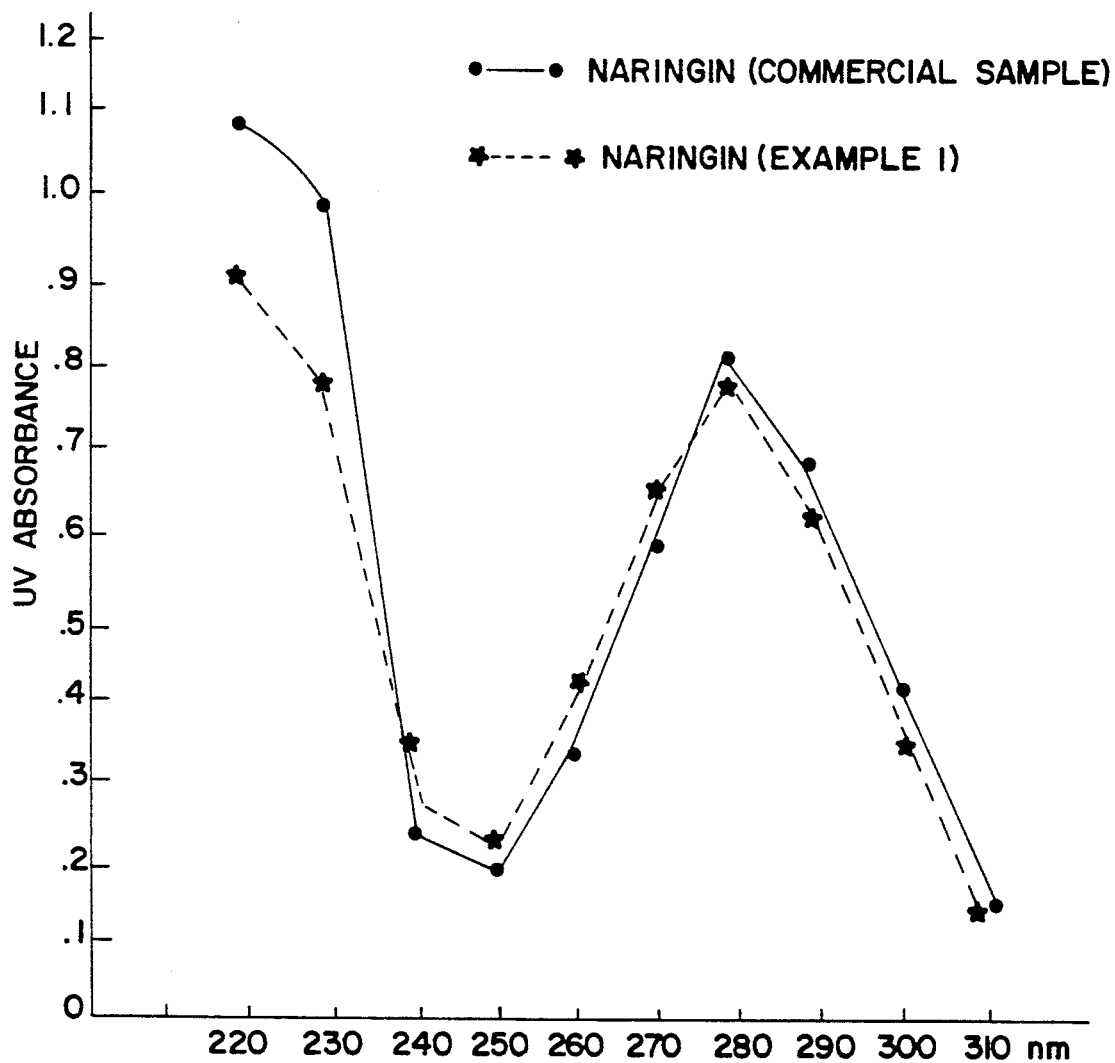
FIG. 1 is the ultraviolet absorption spectrum of naringin commercially available and of naringin prepared by the method of this invention.

FIGS. 9a and 9b and 10a, 10b, 10c, and 10d show synergistic action between classical antibiotics and naringin isolated by the described method of the present invention (Example 1). In these FIGS.: 5 FU =5-fluorouracil; JO-1=naringin Example 1; ARA-C=arabinoside cytosine; Endoxan= cyclophosphamide; HU=hydroxy-urea.

FIG. 11 is a drawing of a Table 1 which illustrates the survival of mice bearing cancer cells (lymphoma YC 8), untreated and treated by commercial naringin (i.p. route) and naringin-Example 1.

FIG. 12 is a drawing of a Table 2 illustrates the survival or mice bearing cancer cells (lymphoma YC8), untreated and treated by naringinExample 1 (i.m. route).

FIG. 13 is a drawing of a Table 3 which illustrates the survival of mice bearing cancer cells (Ehrlich carcinoma cells), untreated and treated by naringin according to Example 1 (i.p. route).

FIG. 14 is a drawing of a Table 4 which illustrates the survival of mice bearing cancer cells (lymphoma YC8), untreated and treated by commercial naringin (i.p. route).

DETAILED DESCRIPTION OF THE INVENTION

Both naringin and naringenin, as well as their derivatives, appear to act in two different ways on DNA of cancer cells. First, they contact or close DNA chains at the point of initiation or chain growth. Second, they contract or close DNA chains during chain elongation. These effects are probably the result of complementary strands of the DNA chain binding to each other through the added naringin or naringenin by covalent and/or hydrogen bonding. The closing of DNA chains of normal cells does not occur. It is believed that these phenomena contribute to or cause the selective inhibition of the growth of cancer cells, and the lack of inhibition of growth or normal cells, caused upon exposure of same to naringin or naringenin. However, I do not wish to be bound by this theory or any theory.

An amount of naringin, naringenin, or esters or salts thereof effective to inhibit the growth, i.e., proliferation, of cancer cells is administered to an animal (by animal include especially mammals, including humans) infected with cancer. A solution of these agents may be introduced intravenously, intraperitoneally, or intramuscularly, or orally as by tablet or capsule, or by rectal route, the physician choosing the manner of administration most suitable under the circumstances.

or humans, the dosages will generally fall within the following limits, but the physician may well go below or above these limits in particular cases.

Per os, i.e., by mouth, 1 to 3 grams agent per day. A naringin-acetone extract can be mixed with cellulose powder after pH is adjusted to neutral and dried at 60° to 70° C. for several hours, then pulverized in a Waring blender and placed in capsules, the concentration being such that about 0.5 gram naringin is present in each capsule. Two to six capsules per day may be used without any inconvenience for several months. The dosages will be about the same for the rectal route.

Naringin may be intramuscularly injected without disturbance into human beings or other animals. For humans, an intra muscular daily dose of 500-1000 milligrams for several consecutive days may be used. The naringin may be used in the form of a solution in small amounts of ethyl alcohol or other solvent such as dimethylsulfoxice (DMSO).

For intravenous injection or perfusion, 250-1000 milligrams daily come will generally be well tolerated. The agent may be dissolved in fresh DMSO and then further diluted with aqueous physiological solution to a final DMSO concentration of.5 to 10 percent.

For intravenous injection, the use of millipore filters as described in Example 1 is necessary. In preparing oral or rectal dosages, it is sufficient to use soluble extract (acetone and/or ether phase) after the pH adjustment to neutral values. In fact there is no toxicity in the commercial syrup used as source for amount. Naringin extract (acetone and/or ether phase) does not exhibit toxic effects on animals. Concentrated naringin extract can be mixed with cellulose powder dried, when pulverized and directly used in capsules in a manner that each capsule contains one appropriate unit dosage amount (oral route), or embodied with wax for this purpose for suppository dosage (rectal route).

For viral infections, dosages of the same order of magnitude as those used in the treatment of cancer will be used; the same modes of administration may be used.

To prevent viral infections of plants or for post infection treatment, the active agent will be applied with a physiologically acceptable carrier, which may be liquid or solid, particularly adapted for adhesion to plant leaves or other paris of the plant (50 to 200 micrograms per leaf).

Extraction of Naringin from Plants

Example 1

Hippophae Rhamnoides

A commercially available syrup for humans containing large amounts of vitamin C and comprising about forty percent sugar and sixty percent extract of berry of the plant *Hippophae Rhamnoides*, was used as starting material. This syrup is available from Laboratories Weeua, 9 rue Eugene-Jung, 68330 Hungue, France.

To 500 millimeters of syrup, hydrochloric acid was added (final concentration 1 N) and the mixture was heated in a beaker for fifteen minutes at 100° C. After cooling the thus-hydrolyzed material, an excess of acetone was added (volume ×3 or 4 ). The mixture was mechanically shaken at room temperature. After a moment of standing, two phases appear. The acetone upper phase (yellow color) was removed and saved. Treatment of aqueous phase with acetone was repeated several times until acetone phase does not contain yellow color. Then several extractions were performed in the same manner with ether in order to extract the maximum of the active agent (naringin and naringenin).

The acetone phases were pooled, and distilled. The ether phases were pooled, and distilled. The distilled solvents may serve for further extractions. The acetone and ether residues were combined and pH adjusted to 7.0 (NaOH or KOH), and constitute highly concentrated naringin.

According to the form which will be given to the agent and the mode of administration, the agent will be or will not be further purified. If one decides on further purification, the acetone/ether residues are dissolved in a mixture of water-ethanol (1:1), the pH adjusted to 10-12 and the material filtered on millipor filters (0.45μ). The material remaining on millipor contains essentially pure naringin/naringenin. The filters were then incubated with 95° ethyl alcohol in a beaker with slight heating. The extraction with ethyl alcohol was repeated several times. The presence of naringin dissolved in the ethanol was determined by UV absorbance at different wavelengths (nm) which gives a characteristic spectrum, shown in FIG. 1. The preparation contains essentially naringin, and naringenin is probably present in small amount. Little or no vitamin C, sugar or lipids remain present in such a preparation.

Comparison with commercially available naringin used as standard (dissolution in ethyl alcohol) is then performed according to several criteria. The spectrum in UV absorption from 220 to 310 nm is determined by using 4 to 20 μg (micrograms) of naringin/milliliter. The spectrum of product isolated according to this Example 1 essentially coincides with that obtained for the reference naringin product. Illustration in FIG. 1. Naringenin has practically the same spectrum with maximum absorption (290 nm) as that of the reference solution.

On chromatography paper or silica gel plates, naringin isolated in this Example 1 migrates in the presence of ethanol as solvent, as does commercial naringin. Spots of both detected by UV light are in both cases close to the front of the solvent.

The same extraction and purification procedure has been applied directly to the Hippophae fruit.

The preparation of this Example 1 is more soluble in water and possesses a better biological activity compared with that exhibited by commercial compounds. This difference is probably due to the presence of small quantities of remaining sugars or lipids in the preparation.

Naringin prepared by the method illustrated in this Example has been given the name of "JO-1," and tests were done under that name.

Example 2

Citrus

Green lemon skin was peeled off and mixed with water and broken with a mixer. For isolation of naringin, the same procedure as above Example 1 was used. Certain grapefruits and oranges can also be used as a source for extraction of naringenin and naringin.

Example 3

Endive roots (*Chicorum endivia*)

Endive roots grown in earth are washed then peeled off and the peel not conserved. The roots are washed, cut into pieces and crunched with water in order to get an heavy soup-like mixture which is boiled for 30 min. at 100° C. The liquid is then filtered through a piece of woven material, vegetal fragments are re-extracted several times under the same conditions. The filtered liquids are pooled, concentrated and hydrolysed with hydrochloric acid (final concentration 1 N) for 10 min. at 100° C., then cooled. All other steps for purification are the same as those described above in Example 1.

Effects of Naringin and Naringenin

Example 4

The effect of naringin and naringenin has been detected according to an in vitro method which shows the action of a given substance on the replication process of DNA originating from either normal tissues or cancer tissues, as described in French patent application No. 7,728,208 of Sept. 19, 1977, which corresponds to U.S. Pat. No. 4,264,729 issued Apr. 28, 1981.

Figure 3:
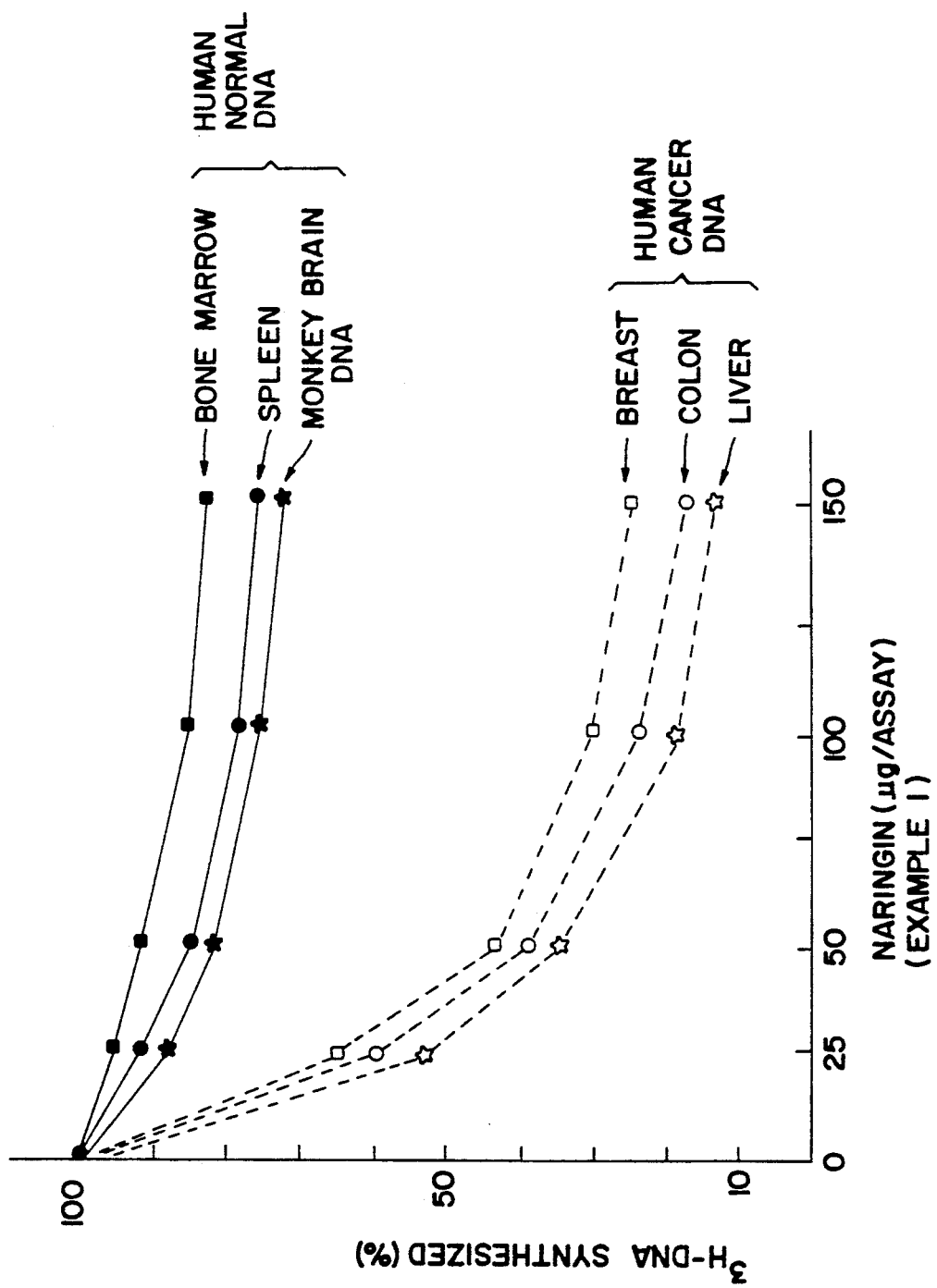
FIG. 3 shows the effect of naringin on the in vitro synthesis of DNA from normal cells and from cancer cells.

Results for naringin are presented in FIG. 3. They show that this product strongly inhibits in vitro synthesis of DNAs from different human cancer tissues, i.e. breast, colon and liver cancers, while that of DNAs from normal tissues (human bone marrow and spleen and monkey brain) is practically unaffected. This shows that naringin specifically interferes with cancer DNA but not with DNA polymerase. The same is true for naringenin. DNAs used were isolated from human cancer and normal tissues furnished by different hospitals as indicated in IRCS Medical Science 14: 809-810, 1986. The normal brain tissue originated from *Macaca mulatta*.

Example 5

The same test method was used on DNA from cancerous tissue, determining the amount of tritium-labeled DNA synthesized over a period of time and the effect of introducing naringin at different points in time. The results, illustrated in FIGS. 4a and 4b, show that naringin acts on DNA initiation sites when given at zero time of incubation, and also stops DNA chain elongation if added after the reaction starts.

Example 6

Figure 5A:
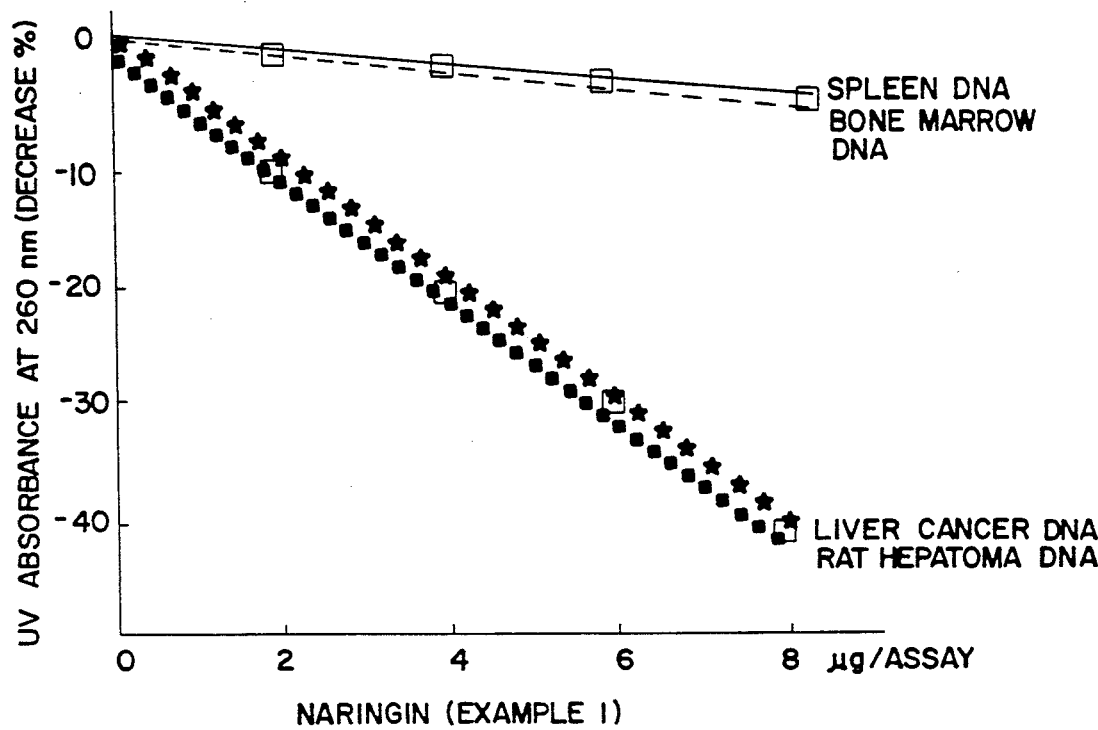
FIGS. 5a and 5b shows the effect of naringin, and of naringenin, in contracting cancer cell DNA chains but not contracting normal DNA chains, the extent of contraction being shown by hypochromicity.
Figure 5B:
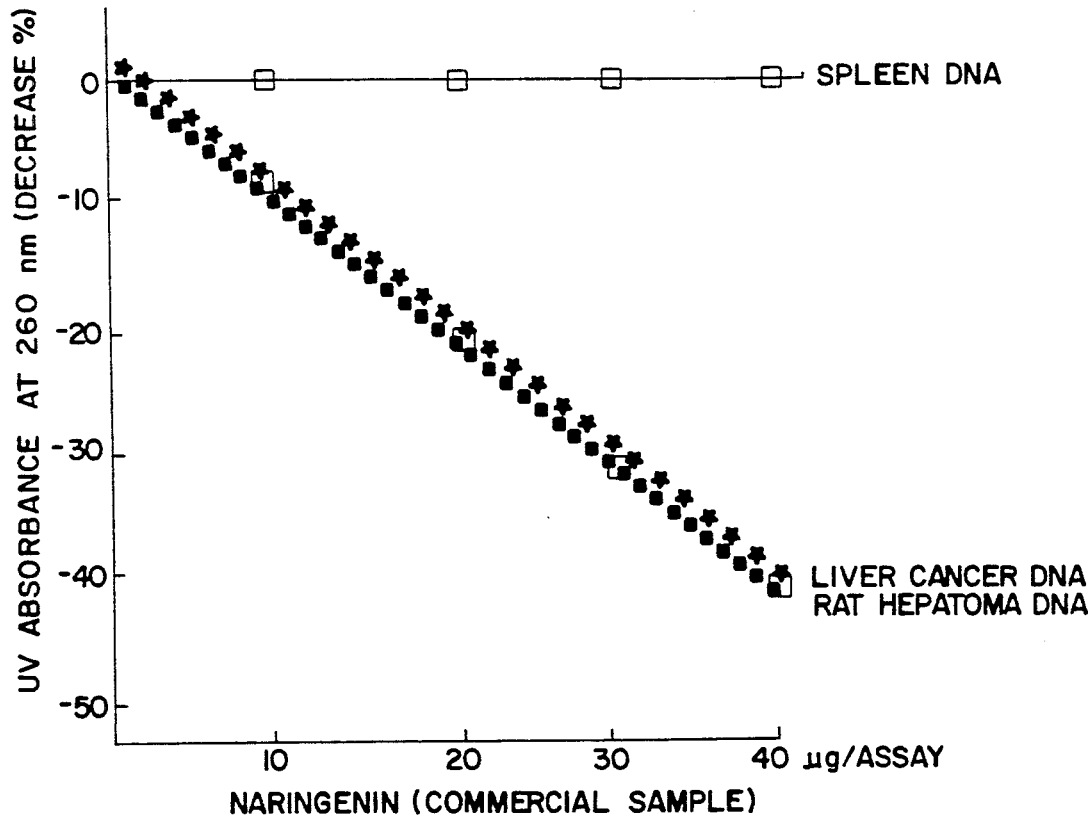

Naringin prepared in accordance with Example 1, and a commercial sample of naringenin prepared by Roth Co. of France, were used for comparison. The results of tests conducted as described below, displayed in FIGS. 5a and 5b show that both materials contract cancer cell DNA chains but have either no effect or a very slight effect on normal cell DNA. The results are expressed as decrease of UV absorbance (hypochromicity) in the presence of various concentrations of the agent. The hypochromicity corresponds to DNA chain contraction, while hyperchromicity would correspond to DNA chain opening (i.e. the breaking of hydrogen bonds which normally hold the two DNA chains together). The spleen and bone marrow DNAs used in this test were from normal human spleen and bone marrow tissue cells.

UV absorbance at wavelength of 260 nm for different DNAs from normal and cancer cells is performed at room temperature. 20 μg (micrograms) of DNA (deoxyribonucleic acid) are dissolved in 1 ml of Tris-HC1 buffer ($10^{-2}$ molar, pH adjusted to 7.3, solution made using sterile distilled water). The absorbance is measured before and after addition of either naringin or naringenin. The blank cuvette contains an equivalent amount of naringin or naringenin, but not DNA. The contact between DNA and compound is of about one minute (very slight agitation). The absorbance at 260 nm is then measured. The results are expressed as diminution (%) of UV absorbance.

Example 7

Naringin prepared in Example 1 has been used for determining its effect on in vitro cultured human cancer and normal cells, according to the method of Shoermaker R.H. et al., Cancer Research 45: 2145-2153, 1985). Culture medium contained 100 μg of penicillin and streptomycin in order to prevent bacterial contamination.

Figure 2:
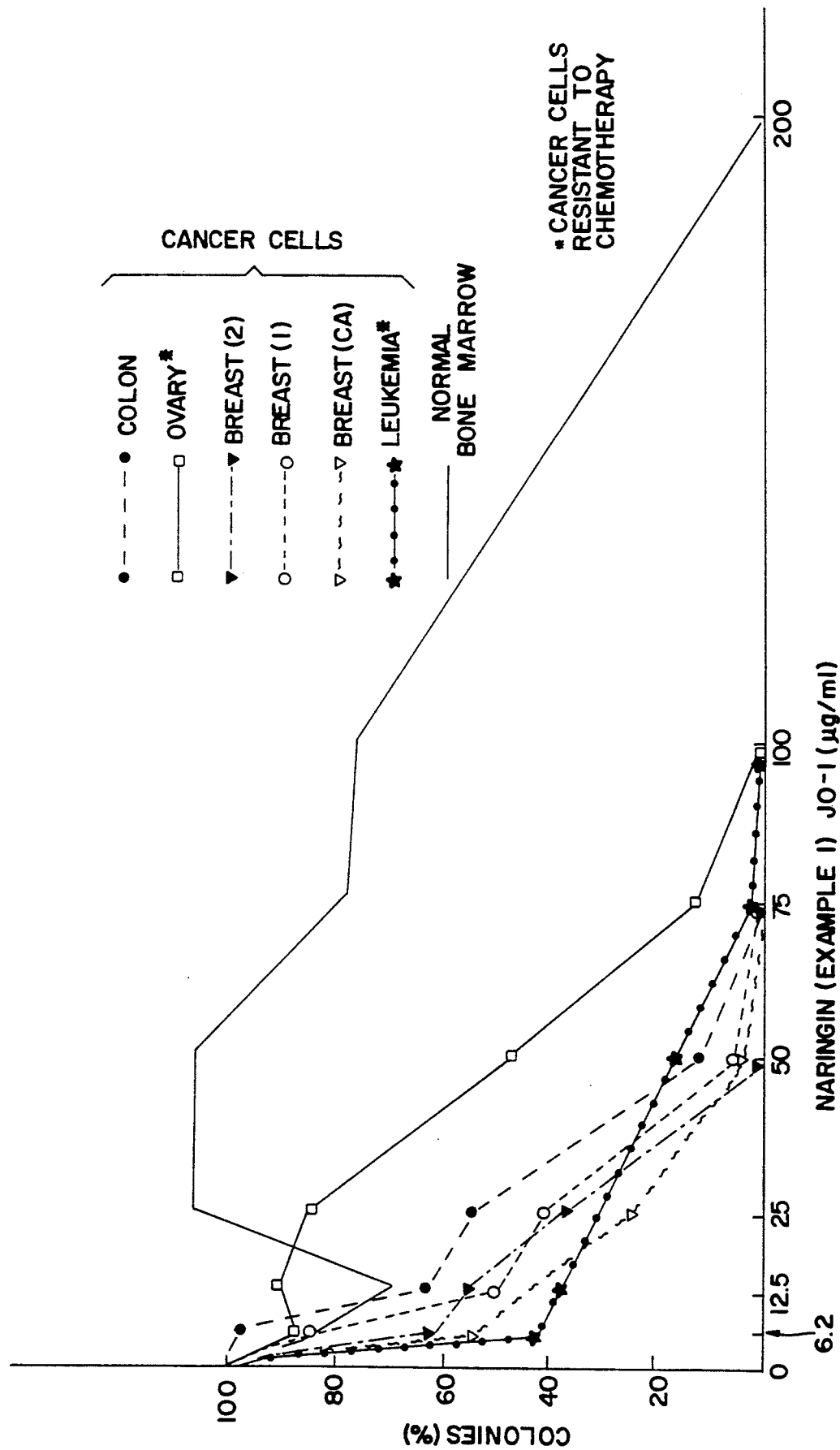
FIG. 2 shows the effects of naringin when tested using in vitro cultured human cancer and normal cells.

FIG. 2 shows results of this test, demonstrating the differential effect of various concentrations of naringin. Naringin strongly inhibits the various human cancer cells and has little effect on normal human bone marrow cells, and this in spite of a great sensitivity possessed by hematological cells to the effect of chemotherapeutic agents in general.

It is important to note that the ovary cancer cells* and leukemic cells* used in this Example were resistant to classical chemotherapy.

These results would indicate that naringin may sensitize cells resistant to chemo/radiotherapy by conventional therapeutic agents and, in all cases, these cells may be destroyed by using naringin and/or naringenin or their derivatives.

Example 8

Figure 7:
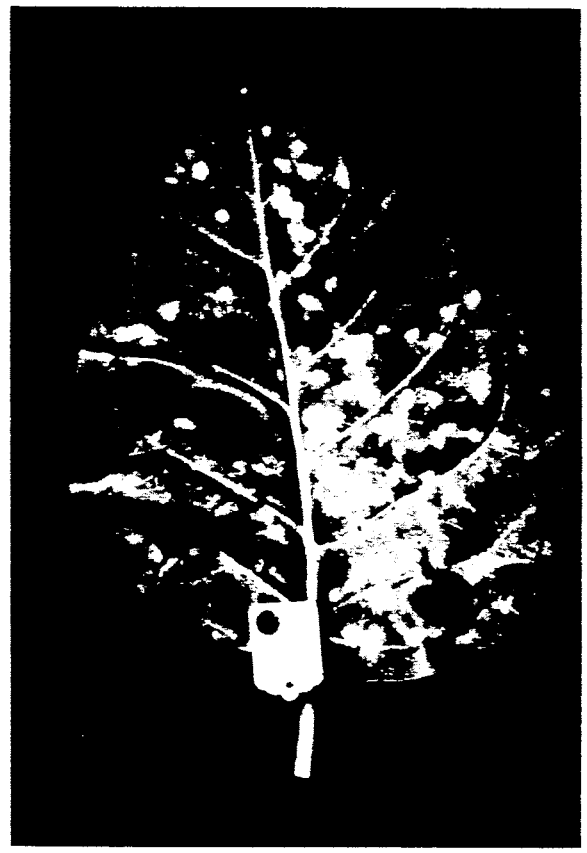
FIG. 7 shows a tobacco leaf infected with tobacco mosaic virus (TMV), one side of the leaf having been treated with naringin and the other side not treated.

The effect of naringin prepared according to Example 1, of commercial naringin and of commercial naringenin has been tested on tobacco mosaic virus (TMV). In this experiment, viral suspension containing 2 μg of virus/ml of distilled water, was incubated at 30° C. for 30 min. with each of the above compounds (20-50 micrograms per milliliter) and then 20 μl placed on one-half of the leaf (xanthy tobacco) while the same concentration of untreated virus was placed on the other half of the same leaf. The appearance of viral disease was checked two to three days later. By counting the "plaque" forming units (PFU), each corresponding to about 10 viral particles, it was observed that each of the added agents inhibits TMV multiplication. FIG. 7 shows the results of the test with naringin from Example 1. Naringenin or commercial naringin gave similar results.

Example 9

Both naringin and naringenin inhibit in vitro the activity of Terminal deoxynucleotidyl Transferase (TdT), an enzyme involved in the integration of viral genome into host cell. This enzyme is present in cat leucosis vaccine prepared by genetic engineering (Engerix® Leucocell vaccine), vaccine highly purified. I have previously shown that this enzyme catalyzes the polymerisation of d-TMP and d-CMP originating from d-TTP and d-CTP used respectively as substrates.

Figure 6:
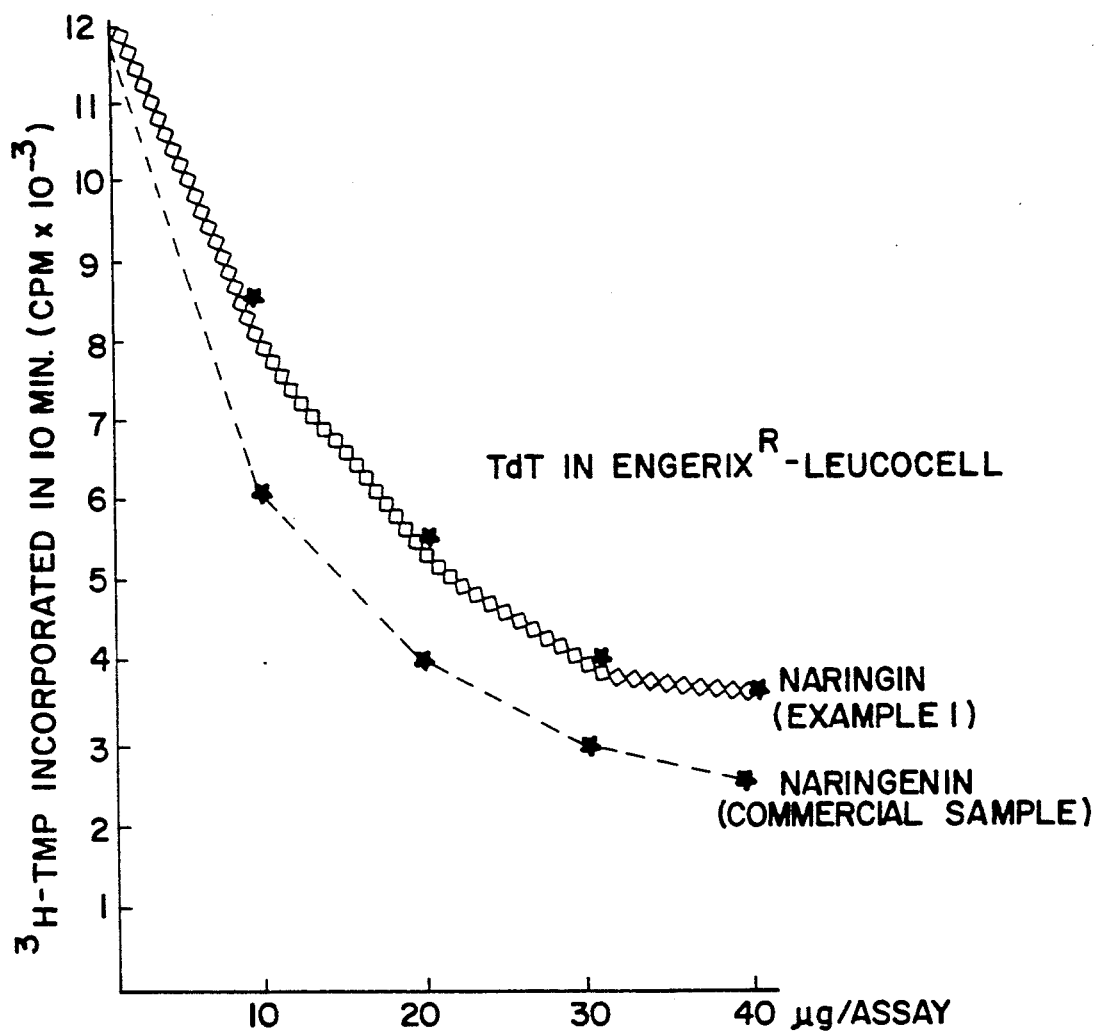
FIG. 6 shows the effect or naringin and of naringenin on the activity of Terminal deoxynucleotidyl Transferase (TdT).

For testing the activity of TdT, the incubation medium (0.10 ml final volume) contains: 25 μmoles fresh solution of Tris-HCl buffer pH 7.70; 2 μmoles MgCl$_2$; ($^3$d-NTP (deoxynucleoside-5'-triphosphate, 100,000 CPM). Increasing amounts of Leucocell vaccine (as indicated in FIG. 6) are used. Incubation for 10 minutes at 36° C., then addition of an equal volume of trichloroacetic acid (TCA 5%). Acid-precipitable material is filtered on millipore (Whatman GF/C), washed with 5% TCA then with 95° alcohol. After millipore drying, radioactivity of acid-insoluble material is measured in scintillation spectrometer Packard. The results are expressed as CPM (counts/minute)/sample.

FIG. 6 shows that both naringin and/or naringenin inhibit in vitro activity of TdT which contaminates commercial vaccine prepared from an RNA virus responsible for cat leucosis. In contrast, the activity of TdT which contaminates Engerix®-vaccine antigen B (Med. Sci. Res. 1987, vol.15 pp. 529–530), an antigen prepared from DNA virus is not inhibited, under the same conditions, by naringin or naringenin. Thus both naringin and naringenin selectively interfere with the proliferation of RNA virus but not DNA virus. However, as RNA from RNA-virus is transcribed into DNA by reverse transcriptase before being integrated into cell genome (potential role of TdT), naringin and naringenin are equally useful agents in treatment of all DNA infections equally.

Example 10

The effect of naringin on in vitro reverse transcriptase activity was determined. The reverse transcriptase commercially available from erythroblastosis virus (RNA virus) was used. The test was carried out as follows:

The reaction mixture (150 μl, final volume) contained 25 μM Tris-HCl buffer, pH 7.7; 2 μM MgCl$_2$; 0.6 nM/each of deoxyribonucleoside-5'-triphosphates: deoxyadenosine-triphosphate (dATP), deoxycytidine-triphosphate (dCTP), deoxyguanosine-triphosphate (dGTP) and 0.6 nM $^3$H-thymidine triphosphate ($^3$H-TTP, 100,000 CPM); 0.2–0.5μg globin m RNA (freshly prepared solution pH 6.5); 0.1 μg oligo dT$_{12-18}$ and 1–5 μg enzymatic protein. After 10 minutes incubation at 37° C. the reaction was stopped by adding an equal volume of cold trichloroacetic acid (TCA 10%) containing 0.02 M sodium pyrophosphate. The precipitate was filtered on glass filter Whatman (GF/A or GF/C), washed with 5% TCA containing 0.02 M pyrophosphate, then with ethyl alcohol 95° and finally dried. The radioactivity was measured in 5 ml of scintillation fluid with Beckman spectrometer. The radioactivity of acid precipitable material was determined.

The following table indicates the rate of inhibition when naringin of Example 1 is present in the incubation reaction in the presence of globin m RNA.

|  | CPM of 3H-TMP incorporated in 10 min. | % inhibition |
| --- | --- | --- |
| complete mixture | 1676 | — |
| + naringin 25 μg | 836 | 50 |
| 50 μg | 520 | 70 |
| 150 μg | 501 | 71 |

EXAMPLE 11

This example illustrates the absence of toxicity of naringin or naringenin injected by intravenous route to BALB C mice. The fragility of mice veins did not permit to practice more repeated injections, either for toxicity or for tumor treatment by this route.

| Naringin (or Naringenin) i.v. Route (10% DMSO) (Example 1) | |
| --- | --- |
| 125 mg/kg | no toxic effect |
| 250 mg/kg | no toxic effect |
| 500 mg/kg | no toxic effect |

One can conclude that naringin and naringenin may be administered either by i.v. injection or by perfusion at doses from 250–1000 mg/kg, doses well tolerated.

Example 12

The low affinity of naringin for normal cell DNA on one hand, for cells in vitro culture on the second hand, as well as the absence of toxicity in mice, are facts which suggest an absence of toxicity towards blood cells, white blood cells and platelets in particular.

A solution of naringin (Example 1) (10% DMSO in physiological solution) was injected (50 mg) to rabbits three times per week by intravenous route for two consecutive months. No change in blood analysis of animals treated in that way was detected, neither a loss of body weight.

Example 13

O BALB C mice bearing lymphoma YC8 (ascitic form) and Swiss mice bearing Ehrlich ascitic cells (20–22 grams, Charles River breeding) were distributed at random in sets of 10.

Each set received respectively:
Set I Control. Received tumor cells and NaCl isotonic solution (0.2 ml/mouse, twice/day, i.p. route)
Set II: Mice bearing tumor cells received JO-1 (= naringin, Example 1): 0.2 ml/mouse, twice/day, i.p. route (for JO-1 concentrations, see Tables 1, 3, and 4, and FIG. 10.)
Set III: Mice bearing tumor cells received naringin (JO-1): 0.2 ml/mouse twice/day (for concentrations, see FIGS. 9 and 10), i.p. route and, at the same time these mice received a chemotherapeutic agent (for concentrations, see FIGS. 9 and 10) i.p. route.

Set IV: Mice bearing tumor cells received naringin (Example 1): 0.2 ml/mouse twice/day (for concentrations, see Table 2), i.m. route.

Ascitic tumor cells were taken in sterile medium from mice bearing these cells for 15-20 days. 0.1 ml of ascitic suspension was mixed with 10 ml of buffered solution (pH 7.2) : (NaCl 7.2 g/l; $Na_2HPO_4$ 4.3 g/l and $KH_2PO_4$ 0.4 g/l).

The number of cells was determined (by Malassez cell) and cellular suspension diluted in order to get cell number close to 40.000-50.000/ml. 0.1 ml of this suspension was immediately injected by i.p. route to mice in sets I, II and III and by i.m. route to mice in set IV.

Treatment: 48 hours after injection of tumor cells: the mice of set II received (i.p.) JO-1 heated at 37° and filtered on millipore, treatment for five consecutive days; the mice of set III were treated (i.p.) by a mixture of JO-1 and one of the antibiotics for 5 consecutive days; the mice of set I (control) received (i.p.) only isotonic solution for 5 consecutive days; the mice of set IV received (i.m.) JO-1 for 15 consecutive days.

Mice were observed for one month or two months after cessation of treatment. Only the survivors in excellent physical condition were taken into consideration.

It should be noted that Ehrlich ascitic cells are less sensitive to the effect of naringin than lymphoma YC8 cells.

What is claimed:

1. A method of inhibiting the growth of cancer cells sensitive to naringin which comprises contacting such cells with an effective concentration of naringin.

2. A method of inhibiting the growth of cancer cells sensitive to naringenin which comprises contacting such cells with an effective concentration of naringenin.

3. A method of treating a mammal infected with cancer cells which comprises administering to said mammal naringin thereto in an amount such that the growth cancer cells sensitive to naringin is inhibited to a greater extent than the growth of normal haemopoietic cells is inhibited.

4. A method of treating a mammal infected with cancer cells which comprises administering to said mammal naringenin thereto in an amount such that the growth of cancer cells sensitive to naringin is inhibited to a greater extent than the growth of normal haemopoietic cells is inhibited.

5. A method according to claim 3 wherein said cancer cells are resistant to chemotherapy or radiotherapy.

6. A method according to claim 4 wherein said cancer cells are resistant to chemotherapy or radiotherapy.

7. A method for selectively contracting DNA chains of cancer cells while not contracting DNA chains of normal human bone marrow or spleen cells which comprises contacting a biological system containing both such chains with an effective concentration of naringin.

8. A method for selectively contracting DNA chains of cancer cells while not contracting DNA chains of normal human bone marrow or spleen cells which comprises subjecting a biological system containing both such chains to the action of an effective concentration of naringenin.

* * * * *